(12) United States Patent
Dodey et al.

(10) Patent No.: US 6,316,413 B1
(45) Date of Patent: Nov. 13, 2001

(54) PEPTIDE AGONISTS OF BRADYKININ $B_2$ RECEPTOR

(75) Inventors: Pierre Dodey, Fontaine-lés-Dijon; Jean-Michel Luccarini, Dijon; Jean Martinez, Saussan; Muriel Amblard; Isabelle Daffix, both of Montpellier, all of (FR)

(73) Assignee: Fournier Industrie et Sante, Paris (FR)

( * ) Notice: Subject to any disclaimer, the term of this patent is extended or adjusted under 35 U.S.C. 154(b) by 0 days.

(21) Appl. No.: 09/319,417

(22) PCT Filed: Dec. 3, 1997

(86) PCT No.: PCT/FR97/02193

§ 371 Date: Jun. 4, 1999

§ 102(e) Date: Jun. 4, 1999

(87) PCT Pub. No.: WO98/24809

PCT Pub. Date: Jun. 11, 1998

(30) Foreign Application Priority Data

Dec. 4, 1996 (FR) .................................................. 96 14890

(51) Int. Cl.[7] .............................. C07K 7/18; C07K 5/078; A61K 38/10; A61K 38/08; A01N 43/00
(52) U.S. Cl. ............................ 514/16; 514/183; 530/323; 530/328; 544/49; 544/105
(58) Field of Search ..................... 514/16, 183; 530/323, 530/328; 544/49, 105

(56) References Cited

U.S. PATENT DOCUMENTS 4,477,464 10/1984 Slade .
4,512,988 4/1985 Weller .
5,491,084 2/1996 Karanewsky .

FOREIGN PATENT DOCUMENTS

| 3423743 | 10/1995 | (DE) . |
| 0322 779 | 5/1989 | (EP) . |
| 413277 | * 11/1990 | (EP) . |
| WO9507294 | 3/1995 | (WO) . |
| WO 9524422 | 9/1995 | (WO) . |

* cited by examiner

Primary Examiner—Michael Borin
(74) Attorney, Agent, or Firm—Carmen Pili Ekstrom

(57) ABSTRACT

The invention concerns a pseudopeptide compounds selected among the set constituted by:

(i) the compounds of formula (I):

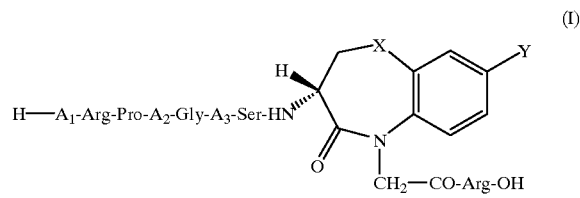

in which:
  $A_1$ represents a single bond, D-Arg or L-Lys;
  $A_2$ represents L-Pro or trans-4-hydroxy-L-Pro (4Hyp);
  $A_3$ represents L-Phe or L-thienylalanine (Thi);
  Y represents a hydrogen atom or a $C_1$–$C_3$ alkyl group;
  X represents a sulphur or oxygen atom; and, (ii) their additive salts. The invention also concerns the preparation and use of this compound and its additive salts in therapy.

19 Claims, No Drawings

PEPTIDE AGONISTS OF BRADYKININ B₂ RECEPTOR

FIELD OF THE INVENTION

The present invention relates to novel compounds of the peptide type or an analogous type, to their method of preparation and to their use in therapeutics. These novel compounds, called "pseudopeptides", have an action of the bradykinin $B_2$ receptor agonist type and are useful in therapeutics, especially for the treatment of pathological conditions of the cardiovascular system.

PRIOR ART

It is known that, through its action on the $B_2$ receptor, bradykinin, a peptide composed of 9 amino acids (Arg-Pro-Pro-Gly-Phe-Ser-Pro-Phe-Arg), has beneficial effects in the treatment of certain pathological conditions, especially in the cardiovascular system. Thus bradykinin protects the heart from myocardial ischemia and prevents certain deleterious events associated with reperfusion of the ischemic heart (cf. the article by L. E. RUBIN et al., Circ. Res., 76, 434–440, 1995, and the article by T. J. M. TOBE et al., J. Cardiovasc. Pharmacol., 17, 600–607, 1991).

Bradykinin also makes it possible to increase the permeability of the blood-brain barrier and thereby to promote the passage of anti-infectious or antitumoral drugs (T. INAMURA et al., J. Cerebral Blood Flow and Metab., 14, 862–870, 1994; FR-M-7979). Bradykinin has also been described as causing the triggering of uterine contractions (T. ENGSTROM et al., J. Endocr., 118, 81–85, 1988), as being capable of inducing ovulation (Y. YOSHIMURA et al., Endocrinology, 122, 2540–2546, 1988) and as being capable of increasing spermatozoal motility (W. MISKA et al., Arch. Androl., 33, 1–5, 1994).

Bradykinin is of no practical use because its rapid degradation by proteases limits its duration of action. It was therefore desirable to find compounds which were of the bradykinin $B_2$ receptor agonist type, i.e. had an action similar to that of bradykinin, but which were not susceptible to degradation by proteolytic enzymes. For this purpose WO-A-89/09231 proposed bradykinin derivatives obtained by reduction of one of the amide linkages. Other modified structures derived from bradykinin and again containing reduced amide linkages were proposed in U.S. Pat. No. 5,112,596 and U.S. Pat. No. 5,268,164, which relate to their property of increasing the permeability of the blood-brain barrier; one of these compounds, RMP7, is currently undergoing a clinical trial in order to evaluate its ability to potentiate the action of anticancer drugs in patients suffering from cerebral gliomas.

It is further known that WO-A-95/07294 and WO-A-95/24422 each recommend peptides and pseudopeptides as bradykinin receptor antagonists. Now, these peptides and pseudopeptides happen to be structurally different from the compounds according to the invention of formula I below.

It is also known that EP-A-0322779 proposes 5-oxo-1,5-benzothiazepin-1-acetamide derivatives and 5-oxo-1,5-benzooxazepin-1-acetamide derivatives as antiamnesic agents.

These derivatives are found to be structurally different from the pseudo-peptides of formula I according to the invention.

OBJECT OF THE INVENTION

According to the invention it is proposed to provide a novel technical solution for overcoming the above-mentioned disadvantages associated with the use of bradykinin. This novel solution involves compounds acting as bradykinin $B_2$ receptor agonists, i.e. having an action similar to that of bradykinin. These compounds have a novel structure which is different from that of bradykinin and the known analogous products of the prior art. These compounds are potentially resistant to the action of proteases and hence have a duration of action compatible with use in therapeutics.

In accordance with this novel technical solution, it is proposed according to a first feature of the invention to provide compounds of the pseudopeptide type as novel industrial products, according to a second feature of the invention to provide a method of preparing these compounds, and according to a third feature of the invention to provide the use of these compounds, especially in therapeutics, for example as active ingredients for increasing the permeability of the blood-brain barrier, improving genital functions and treating myocardial ischemia.

SUBJECT OF THE INVENTION

In accordance with the novel technical solution of the invention, a compound of pseudopeptide structure is recommended as a novel industrial product, said compound being characterized in that it is selected from the group consisting of:

(i) the compounds of formula I:

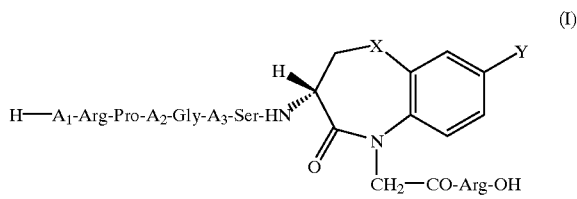

(cf. SEQ ID No. 1 and 2)
in which:
$A_1$ is a single bond, D-Arg or L-Lys,
$A_2$ is L-Pro or trans-4-hydroxy-L-Pro (4Hyp),
$A_3$ is L-Phe or L-thienylalanine (Thi),
Y is a hydrogen atom or a $C_1$–$C_3$-alkyl group, and
X is a sulfur or oxygen atom; and
(ii) their addition salts.

In the sequence listing given below, SEQ ID No. 1 relates to the products of structure I in which $A_1$ is a single bond, and SEQ ID No. 2 relates to those of structure I in which $A_1$ is D-Arg or L-Lys.

According to the invention a method of preparing a compound of formula I and its addition salts is also recommended. The characteristics of this method are given below.

The use of a compound of formula I or one of its non-toxic addition salts is also recommended for obtaining a drug for use in therapeutics in the treatment of pathological conditions where bradykinin brings a beneficial effect, especially in the cardiovascular system, for example for treating myocardial ischemia or improving the permeability of the blood-brain barrier, or in the genital system, for example for triggering ovulation, improving spermatozoal motility or triggering uterine contractions.

The compounds of formula I and their addition salts are also useful as reagents in biological assays.

Abbreviations

For the sake of convenience, the following abbreviations and acronyms have been used in the present text:

a) for the amino acids and their residues:
Ala alanine
Arg arginine
DBO(Y) is a "pseudo" amino acid of the structural formula

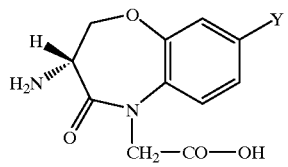

(where Y is as defined above)
DBT(Y) is a "pseudo" amino acid of the structural formula

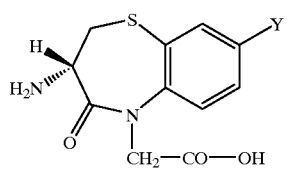

(where Y is as defined above)
DBZ(Y) is DBO(Y) or DBT(Y), where Y is as defined above
Gly glycine
4Hyp trans-4-hydroxyproline [alternative nomenclature for the product of L configuration: (2S,4R)-4-hydroxypyrrolidine-2-carboxylic acid]
Phe phenylalanine
Pro proline
Ser serine
Thi thienylalanine [alternative nomenclatures: 3-(thien-2-yl) alanine or ThAla]
(b) for the other moieties:
Adoc adamantyloxycarbonyl
Aoc t-amyloxycarbonyl
Boc t-butoxycarbonyl (or 1,1-dimethylethoxycarbonyl)
BOP benzotriazol-1-yloxytris(dimethylamino)phosphonium hexafluoro-phosphate
Bzl benzyl (or phenylmethyl)
DCM dichloromethane
DIEA diisopropylethylamine
DMF N,N-dimethylformamide
Fmoc fluoren-9-ylmethoxycarbonyl
Foc fufuryloxycarbonyl
HTFA trifluoroacetic acid
Iboc isobornyloxycarbonyl
Res resin
RT room temperature (15–20° C.)
THF tetrahydrofuran
Tos p-toluenesulfonyl (or tosyl)
z phenylmethoxycarbonyl (or benzyloxycarbonyl)
Z(p-Cl) p-chlorobenzyloxycarbonyl
Z(p-OMe) p-methoxybenzyloxycarbonyl

DETAILED DESCRIPTION OF THE INVENTION

Hereafter, when an amino acid contains an asymmetric carbon atom (in the present case, any amino acid other than Gly), the natural L configuration is omitted and only the unnatural D configuration is specified.

As far as DBZ(Y) is concerned, it should be pointed out that the carbon in the 3-position, carrying the amine group, has the S configuration when X is a sulfur atom and the R configuration when X is an oxygen atom (in accordance with the Cahn-Ingold-Prelog rules of absolute configuration).

In practical terms, with the exception of Gly and of $A_1$=D-Arg, all the amino acids of the pseudopeptide of formula I have the L configuration.

Addition salts are understood as meaning every acid addition salt obtained by reacting a compound of formula I with a mineral acid or an organic acid. The preferred mineral acids for salifying the basic compound of formula I are hydro-chloric, hydrobromic, phosphoric and sulfuric acids. The preferred organic acids for salifying the basic compound of formula I are methanesulfonic, maleic, fumaric, oxalic, citric, acetic and trifluoroacetic acids.

$C_1$-$C_3$-alkyl group is understood here as meaning a methyl, ethyl, propyl or isopropyl group.

The method of preparing a compound of formula I which is recommended according to the invention comprises the steps consisting in:
(1) reacting ethyl bromoacetate with a compound of formula II:

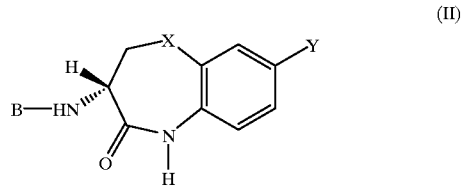

(II)

in which:
X is an oxygen atom or a sulfur atom,
B is an amino-protecting group of the oxycarbonyl type, and
Y is defined as indicated above,
in an inert solvent (especially THF), in the presence of a base (especially KOH), if
necessary using a phase transfer catalyst, at RT and for 1 to 8 hours, to give a compound of formula III:

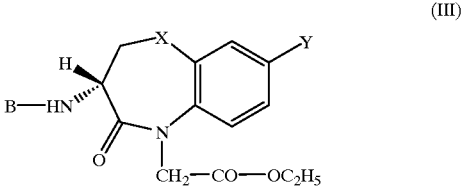

(III)

in which B, X and Y are defined as indicated above;
(2) deprotecting the amine group of the resulting compound of formula III by reaction with hydrogen in the presence of a hydrogenation catalyst, for example palladium on charcoal or on barium sulfate, in a solvent, for example ethanol, at a temperature close to room temperature and under a hydrogen pressure of about $10^5$ to $5.10^5$ Pascals, to give a compound of formula IV:

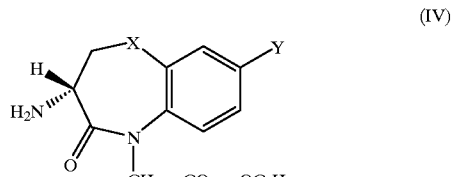

(IV)

in which X and Y are defined as indicated above;

3) reacting the resulting compound of formula IV with an L-serine derivative of formula V:

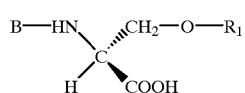
(V)

in which:

B is defined as indicated above and is advantageously Boc, and $R_1$ is a hydroxyl-protecting group sensitive to hydrogenation, especially Bzl, in an inert solvent, especially DMF, in the presence of activators such as BOP and a tertiary amine (especially N-methylmorpholine), at a temperature identical to or close to RT and for 1 to 10 hours, to give a compound of formula VI:

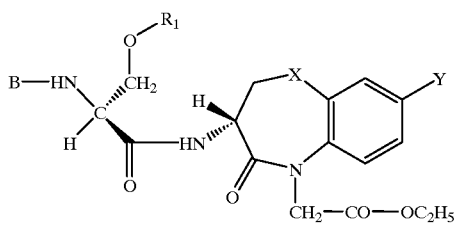
(VI)

in which X, $R_1$, B and Y are defined as indicated above;

(4) hydrolyzing the ethyl ester group of the resulting compound VI by treatment with NaOH (preferably 1 N sodium hydroxide solution) in a solvent such as ethanol, at a temperature identical to or close to RT and for 1 to 5 hours, to give the compound of formula VII:

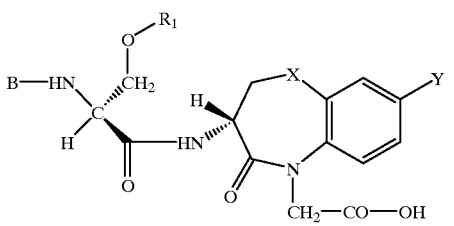
(VII)

in which X, $R_1$, B and Y are defined as indicated above;

(5) reacting the resulting compound of formula VII with a Merrifield resin functionalized by an L-arginine (in which the basic side-group of Arg is protected by a tosyl group, the Arg residue being bonded to the resin by its C-terminal acid group), the reaction being carried out in the heterogeneous phase, in the presence of an appropriate solvent (especially DCM), in the presence of coupling agents customarily used in peptide synthesis (especially BOP and DIEA), at RT, for 1 to 4 hours, to give the grafted resin product of structure VIII:

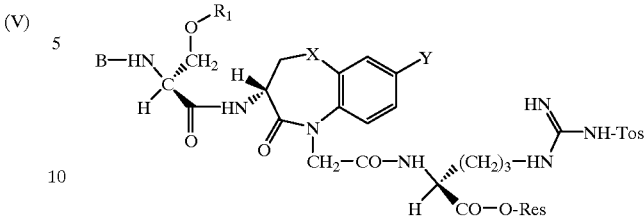
(VIII)

[alternative nomenclature: B-Ser($R_1$)-DBZ(Y)-Arg(Tos)-O-Res]

in which:

X is S or O,

Res is the resin,

B is an amino-protecting group (preferably Boc), $R_1$ is a hydroxyl-protecting group (preferably Bzl), Y is defined as indicated above, and Tos is the tosyl group;

(6) reacting the resulting product of formula VIII, by the known methods of peptide synthesis (especially that known to those skilled in the art as the MERRIFIELD synthesis), with HTFA in DCM to regenerate the amine group at the N-terminal end of the serine, and then with an amino acid whose N-terminal amine group is protected by a group B and whose basic or hydroxyl side-group is protected if such a group is present, and repeating this procedure of deprotection/coupling with the appropriate amino acid as many times as is necessary to obtain the sequence of formula I, namely with the following amino acids in succession:

(α) B-Phe-OH or B-Thi-OH (β) B-Gly-OH (γ) B-Pro-OH or B-4Hyp-OH (δ) B-Pro-OH (ε) B-Arg($R_2$)-OH (ζ) and, if appropriate, B-Lys($R_2$)-OH or B-D-Arg($R_2$)-OH to give one of the desired protected pseudopeptide sequences, especially:

B-D-Arg($R_2$)-Arg($R_2$)-Pro-4Hyp-Gly-Thi-Ser($R_1$)-DBZ(Y)-Arg(Tos)-O-Res,

B-Lys($R_2$)-Arg($R_2$)-Pro-4Hyp-Gly-Thi-Ser($R_1$)-DBZ(Y)-Arg(Tos)-O-Res or

B-Arg($R_2$)-Pro-Pro-Gly-Phe-Ser($R_1$)-DBZ(Y)-Arg(Tos)-O-Res, in which the abbreviations are the same as above and $R_2$ is a protecting group for the basic side-group; and (7) deprotecting and liberating the expected compound by means of a first treatment with trifluoroacetic acid (which removes the protecting group B), followed by a second treatment with hydrogen fluoride, which removes the other protecting groups and liberates the pseudopeptide from the resin to give the expected compound of formula I.

The amino-protecting groups and the hydroxyl-protecting groups which are suitable according to the invention for preparing the compounds of formula I can be selected from the groups known in the field of peptide synthesis, on the one hand for protecting amine or basic groups and on the other hand for protecting hydroxyl groups.

The following may be mentioned in particular among the amino-protecting groups recommended here:

for the temporary protection of the N-terminal end, the groups B of the oxy-carbonyl type such as alkoxycarbonyl, aryloxycarbonyl and heteroaryloxycarbonyl groups, especially Adoc, Aoc, Boc, Fmoc, Foc, Iboc, Z, Z(4-Cl) and Z(4-OMe), and for the basic side-groups (case of Lys and Arg), one of the above groups B, Tos or $NO_2$.

Advantageously the group B used as an amino-protecting group for the N-terminal end will be (i) Z for the products of formulae II and III, and (ii) Boc for the products of formulae V–VIII and in step (6).

Also advantageously $R_2$, the protecting group for the basic side-group if present, will be Z, Tos or $NO_2$.

Preferably $R_1$, the hydroxyl-protecting group for the OH side-groups, will be Bzl.

In the light of the foregoing, the following amino acids will be used very advantageously for the successive couplings of step (6):

(α) Boc-Phe-OH or Boc-Thi-OH (β) Boc-Gly-OH (γ) Boc-Pro-OH or Boc-4Hyp-OH (δ) Boc-Pro-OH (ε) Boc-Arg(Tos)-OH (ζ) and, if appropriate, Boc-Lys(Z)-OH or Boc-D-Arg($NO_2$)-OH.

In step (1) the ethyl bromoacetate can be replaced with another $C_1$–$C_4$-alkyl halogenoacetate, in which the halogeno group is especially Cl, Br or I. Ethyl bromoacetate is the preferred reagent here because of the yield it produces in the preparation of the compound of formula III.

As RT represents a temperature of 15–20° C., a temperature close to RT denotes a temperature between 5 and 30° C. and preferably between 10 and 25° C.

As a variant of the method described above, it is possible to perform the steps consisting in:

(1a) reacting ethyl bromoacetate with a compound of formula II:

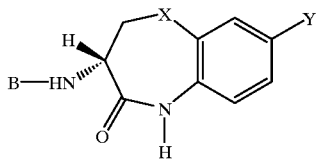
(II)

in which X is S or O, and B and Y are defined as indicated above (B preferably being Boc here), under conditions analogous to those described in step (1) of the previous method, to give the compound of formula III:

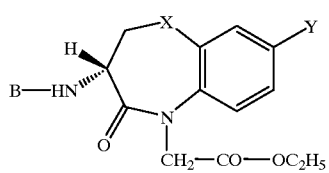
(III)

in which X, B and Y are defined as indicated above;

(2a) carrying out the hydrolysis of the ester group, under conditions analogous to those described in step (4) of the previous method, to give the compound of formula IX:

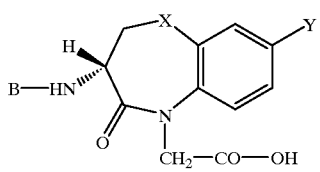
(IX)

in which X, B and Y are defined as indicated above; and (3a) continuing the synthesis of the compounds of formula I, especially by the MERRIFIELD method, as indicated above, the compound of formula IX above being considered as an N-protected amino acid, to give the compounds of formula I after deprotection and separation from the support resin.

Further advantages and characteristics of the invention will be understood more clearly from the following description of Preparatory Examples and results of pharmacological tests.

Of course, these details as a whole do not imply a limitation but are given by way of illustration.

PREPARATION I

Ethyl 3-(S)-[(phenylmethoxycarbonyl)amino]-3,4-dihydro-4-oxo-1,5-benzothiazepin-5(2H)-acetate 7.40 g (0.13 mol) of potassium hydroxide and 3.74 g (0.01 mol) of tetra-butylammonium iodide are added to a solution of 33.27 g (0.1 mol) of 3-(S)-[(phenylmethoxycarbonyl)amino]-2,3-dihydro-1,5-benzothiazepin-4(5H)-one in 300 ml of tetrahydrofuran. After cooling in an ice bath, 16.92 g (0.1 mol) of ethyl bromoacetate are added and the mixture is stirred for 2 hours. When the reaction has ended, the mixture is diluted with water and extracted with ethyl acetate. The organic extraction phases are washed with water, dried over magnesium sulfate and then concentrated under reduced pressure. The yellow oil obtained is purified on silica by flash chromatography using a methylene chloride/isopropyl ether mixture (9/1, v/v) as the eluent. 24.1 g of a pale yellow oil (yield=57.3%) are obtained after evaporation of the solvents.

$[α]_D^{27}=+102°$ (c=1.01; $CHCl_3$)

PREPARATION II

Ethyl 3-(S)-amino-3,4-dihydro-4-oxo-1,5-benzothiazepin-5(2H)-acetate(hydrochloride)

2.24 g ($5.4.10^{-3}$- mol) of the compound obtained according to Preparation I are dissolved in 50 ml of 95% ethanol. 5.4 ml of a 1 M solution of HCl in 95% ethanol are added, followed by 8.1 g of 10% palladium on barium sulfate. The resulting mixture is stirred under a hydrogen atmosphere at atmospheric pressure and at RT for 4 hours. The reaction mixture is then filtered and the solvent is evaporated off under reduced pressure. The residue is resuspended in ethyl ether, then concentrated again under reduced pressure and finally precipitated in ether to give 1.61 g of the expected product in the form of a beige solid (yield=94%). $[α]_D^{23}=+169.9°$ (c=0.76; DMF)

Preparation III

Ethyl 3-(S)-[[2-(S)-(1,1-dimethylethoxycarbonylamino)-3-(phenylmethoxy)-1-oxopropyl]amino]-3,4-dihydro-4-oxo-1,5-benzothiazepin-5(2H)-acetate [Boc-Ser(Bzl)-DBT(H)-OEt]

A solution of 1.52 g ($4.8.10^{-3}$ mol) of the compound obtained according to Preparation II in 15 ml of DMF is prepared and 0.53 ml ($4.8.10^{-3}$ mol) of N-methylmorpholine and 1.56 g ($5.28.10^{-3}$ mol) of 2-(S)-[(1,1-dimethylethoxycarbonyl)amino]-3-(phenylmethoxy) propionic acid [i.e. Boc-L-Ser(Bzl)-OH] are added, followed by 2.33 g ($5.28.10^{-3}$ mol) of BOP and 0.57 ml ($5.28.10^{-3}$ mol) of N-methylmorpholine. After stirring for two hours, 15 ml of saturated sodium bicarbonate solution are added and the mixture is extracted with ethyl acetate. The organic phase is washed with potassium hydrogensulfate solution and then with saturated sodium chloride solution and dried over sodium sulfate. Concentration under reduced pressure gives 2.54 g of the crude product, which is purified by chromatography on silica gel using an ethyl acetate/hexane mixture (1/1, v/v) as the eluent to give the expected product in the form of a white powder (yield=70%).

M.p.=52–54° C.

$[\alpha]_D^{23}$=+150.8° (c=0.85; DMF)

Preparation IV 3-(S)-[[2-(S)-(1,1-Dimethylethoxycarbonylamino)-3-(phenylmethoxy)-1-oxopropyl]amino]-3,4-dihydro-4-oxo-1,5-benzothiazepin-5(2H)-acetic acid [Boc-Ser(Bzl)-DBT(H)-OH]

0.80 g ($1.43.10^{-3}$ mol) of the compound obtained according to Preparation III is dissolved in 15 ml of 95% ethanol, and 2.2 ml of 1 N sodium hydroxide solution are added. After stirring for one hour at RT, the ethanol is partially evaporated off and the residual mixture is taken up with water and washed with ethyl ether. The aqueous phase is acidified with 1 N potassium hydrogensulfate solution and extracted with ethyl acetate. The organic phase is washed with saturated sodium chloride solution and dried over sodium sulfate. After concentration under reduced pressure, the product is precipitated in an ethyl ether/hexane mixture to give 0.70 g of the expected product in the form of a white precipitate (yield=90%).

M.p.=92–94° C.

$[\alpha]_D^{23}$=174.3° (c=0.86; DMF)

Preparation V

Boc-D-Arg(NO$_2$)-Arg(Tos)-Pro4Hyp-Gly-Thi-Ser(Bzl)-DBT(H)-Arg(Tos)-Res

This compound is prepared by MERRIFIELD's solid phase method of peptide synthesis. The starting point is a conventional polystyrene-based MERRIFIELD resin crosslinked with divinylbenzene and functionalized by the grouping Boc-L-Arg(Tos)-OH ($0.41.10^{-3}$ mol/gram). The different components constituting the desired pseudopeptide sequence are introduced one by one using the following cycle:

a) Deprotection of the amine group (protected by the Boc group) by reaction with a solution containing 40% of trifluoroacetic acid and 2% of ethane-dithiol in DCM for 2 min, followed by a washing phase with DCM, then by renewed contact with the above solution for 28 min and finally by washing with DCM, isopropanol and DCM again.
  b) Coupling by reaction with a solution containing the amino acid (protected by a Boc group on its N-terminal amine group and, if appropriate, protected on the reactive groups other than the acid group), BOP and DIEA in DCM and/or DMF. After reaction with an excess of this reactive solution, the resin is washed successively with DCM, methanol and DCM. After the coupling of each new amino acid, a Kaiser test is carried out to check that the reaction has indeed taken place. The coupling reactions are performed using the following reactants in succession (the relative amount reacted, the reaction time and the solvent used are indicated in brackets):

1) Boc-Ser(Bzl)-DBT(H)-OH (1.2 eq., 1 h 40 min, DCM)
2) Boc-Thi-OH [or Boc-(thien-2-yl)alanine] (3 eq., 1 h 30 min, DCM)
3) Boc-Gly-OH (3 eq., 30 min, DCM)
4) Boc-4Hyp-OH [or Boc-4-hydroxyproline] (3 eq., 20 min, DCM)
5) Boc?-Pro-OH (6 eq., 40 min, DCM)
6) Boc-Arg(Tos)-OH [or Nα-Boc-Nω-p-tosyl-L-arginine] (6 eq., 100 min, DCM)
7) Boc-D-Arg(NO$_2$)-OH [or Nα-Boc-Nω-nitro-D-arginine] (3 eq., 1 h, DMF)

The expected pseudopeptide is thus obtained protected and fixed to the MERRIFIELD resin.

The following compounds are obtained grafted onto resin by an analogous procedure:

Preparation VI

Boc-L-Lys(Z)-Arg(Tos)-Pro-4Hyp-Gly-Thi-Ser(Bzl)-DBT(H)-Arg(Tos)-Res

Preparation VII

Boc-Arg(Tos)-Pro-Pro-Gly-Phe-Ser(Bzl)-DBT(H)-Arg(Tos)-Res

Example 1

H-D-Arg-Arg-Pro-4Hyp-Gly-Thi-Ser-DBT(H)-Arg-OH (SEQ ID No. 3)

The resin obtained according to Preparation V is treated with a mixture of trifluoroacetic acid, ethanedithiol and DCM (40/2/60, v/v) and washed with DCM and isopropanol. This first step makes it possible to remove the Boc protecting group carried by the D-Arg residue. The resin is then treated with hydrogen fluoride in the presence of anisole and ethanedithiol at a rate of 1 ml of liquid hydrogen fluoride, 0.1 ml of anisole and 0.05 ml of ethanedithiol to 1 g of resin. After a reaction time of about 1 hour at 0–5° C., ether is added and the resin/pseudopeptide mixture is filtered. The pseudopeptide is then dissolved in an acetonitrile/water mixture and the solution obtained is lyophilized after filtration. The residue is then purified by chromatography on C18 type grafted silica gel, eluting with a solvent gradient ranging from 1% HTFA in water to 1% HTFA in acetonitrile. The fractions containing the expected compound are lyophilized to give the expected compound in the form of its salt with HTFA. The product, which has the appearance of a white flaky solid, is checked by mass spectrometry ($C_{51}H_{77}N_{19}O_{13}S_2$: M=1227).

$[\alpha]_D^{21}$=+6° (c=0.26; CH$_3$OH)

The following compounds are obtained by a procedure analogous to Example 1:

Example 2

H-Lys-Arg-Pro-4Hyp-Gly-Thi-Ser-DBT(H)-Arg-OH (SEQ ID No. 4) $[\alpha]_D^{20}$=−6.4° (c=0.97; H$_2$O)

Example 3

H-Arg-Pro-Pro-Gly-Phe-Ser-DBT(M)-Arg-OH (SEQ ID No. 5) $[\alpha]_D 20=+4.8°$ (c=0.83; $H_2O$)

The following compound is obtained by a procedure analogous to Preparation I:

Preparation VIII

Ethyl 3-(S)-[(1,1-dimethylethoxycarbonyl)amino]-3,4-dihydro-4-oxo-1,5-benzoxazepin-5(2H)-acetate $[\alpha]_D^{23}=+184°$ (c=1; $CHCl_3$)

The following compound is obtained by a procedure analogous to Preparation IV:

Preparation IX 3-(S)-[(1,1-Dimethylethoxycarbonyl)amino]-3,4-dihydro-4-oxo-1,5-benzoxazepin-5(2H)-acetic acid [i.e. Boc-DBO(H)-OH]

$[\alpha]_D^{23}=+179°$ (c=1; DMF)

The following compound is obtained by a procedure analogous to

Preparation V:

Preparation X

Boc-D-Arg($NO_2$)-Arg(Tos)-Pro-4Hyp-Gly-Thi-Ser(Bzl)-DBO(H)-Arg(Tos)-Res

The following compound is obtained by a procedure analogous to Example 1:

Example 4

H-D-Arg-Arg-Pro-4Hyp-Gly-Thi-Ser-DBO(H)-Arg-OH (SEQ ID No. 6) $[\alpha]_D^{20}=-13.55°$ (c=0.86; $H_2O$)

The following compounds are obtained by a procedure analogous to the preparations described by J. SLADE et al. in J. Med. Chem., 1985, 28, 1517–1521:

Preparation XI

R-(5-Methyl-2-nitrophenyl)-N-acetyl-D-cysteine $[\alpha]_D^{21}=-73°$ (c=0.5; $CH_3OH$)

M.p.=172° C.

Preparation XII

R-(5-Methyl-2-nitrophenyl)-D-cysteine $[\alpha]_D^{22}=-151°$ (c=0.36; $CH_3OH$)

M.p.=188° C.

Preparation XIII

R-(5-Methyl-2-nitrophenyl)-N-(phenylmethoxycarbonyl)-D-cysteine $[\alpha]_D^{23}=-21°$ (c=0.34; $CH_3OH$)

M.p.=141° C.

Preparation XIV

R-(5-Methyl-2-aminophenyl)-N-(phenylmethoxycarbonyl)-D-cysteine $[\alpha]_D^{23}=+93°$ (c=0.40; DMSO)

M.p.=175° C.

Preparation XV 3-(S)-[(Phenylmethoxycarbonyl)amino]-3,4-dihydro-8-methyl-4-oxo-1,5-benzothiazepine $[\alpha]_D^{23}=+172°$ (c=0.56; DMSO)

M.p.=77° C.

The following compound is obtained by a procedure analogous to Preparation I:

Preparation XVI

Ethyl 3-(S)-[(phenylmethoxycarbonyl)amino]-3,4-dihydro-8-methyl-4-oxo-l,5-benzothiazepin-5(2H)-acetate $[\alpha]_D^{23}=167°$ (c=0.54; $CHCl_3$)

The following compound is obtained by a procedure analogous to Preparation II:

Preparation XVII

Ethyl 3-(S)-amino-3,4-dihydro-8-methyl-4-oxo-1,5-benzothiazepin-5(2H)-acetate

This product is not isolated and is used directly in the next synthesis step.

The following compound is obtained by a procedure analogous to Preparation III:

Preparation XVIII

Ethyl 3-(S)-[[2-(S)-(1,1-dimethylethoxycarbonylamino)-3-(phenylmethoxy)-1-oxopropyl]amino]-3,4-dihydro-8-methyl-4-oxo-1,5-benzothiazepin-5(2H)-acetate [Boc-Ser(Bzl)-DBT($CH_3$)-OEt]

$[\alpha]_D^{21}=+92.3°$ (c=0.75; DMF)

The following compound is obtained by a procedure analogous to Preparation IV:

Preparation XIX 3-(S)-[[2-(S)-(1,1-Dimethylethoxycarbonylamino)-3-(phenylmethoxy)-1-oxo-opropyl]amino]-3,4-dihydro-8-methyl-4-oxo-1,5-benzothiazepin-5(2H)-acetic acid [Boc-Ser(Bzl)-DBT($CH_3$)-OH]

$[\alpha]_D^{21}=+121.1°$ (c=0.71; DMF)

M.p.=76–78° C.

The following product is obtained by a procedure analogous to Example 1:

Example 5

H-D-Arg-Arg-Pro-4Hyp-Gly-Thi-Ser-DBT($CH_3$)-Arg-OH (SEQ ID No. 7) $[\alpha]_D^{21}=-2.08°$ (c=0.38; $CH_3OH$)

The pharmacological activity of the products according to the invention was evaluated in respect of their ability to bind to the bradykinin $B_2$ receptors and their ability to induce similar effects to those of bradykinin.

The pharmacological activity of the products according to the invention was determined in respect of the ability of the test products to bind to the bradykinin $B_2$ receptor (determination of a Ki on the human $B_2$ receptor cloned and transfected in a stable manner into a CHO cell line) and their ability to induce functional effects comparable to those of bradykinin (determination of a $pD_2$ value on segments of human umbilical vein).

The results obtained from these tests with the compounds according to the invention have been collated in Table I below. The affinity of the compounds for the cloned human $B_2$ receptor is assessed by the value of Ki (concentration expressed in nM) and the induction of functional effects analogous to those of bradykinin is evaluated by the $pD_2$ calculated from the concentrations causing the $B_2$ receptor-dependent contraction of the umbilical vein. The values obtained from these tests with bradykinin are given by way of comparison.

TABLE I

| Product | Ki (nm) | $pD_2$ |
|---|---|---|
| Ex. 1 | 0.7 | 6.7 |
| Ex. 2 | 0.07 | 7.1 |
| Ex. 3 | 12.9 | 6.6 |
| Ex. 4 | 2.5 | 5.1 |
| Ex. 5 | 6 | 7.25 |
| Bradykinin | 0.5 | 7.3 |

The compounds of the present invention, which are bradykinin $B_2$ receptor agonists, are useful in therapeutics in the treatment of pathological conditions for which bradykinin or its homologs exert a beneficial action, for example certain cardiovascular pathological conditions. By way of example, the compounds according to the invention can have a beneficial effect in the treatment of myocardial ischemia or in the prevention of deleterious events associated with reperfusion of the ischemic heart. They can also increase the permeability of the blood-brain barrier, thereby promoting the passage of anti-infectious or antitumoral active principles, or can also enable gene therapy vectors, such as plasmids or naked DNA, to penetrate tissues.

The compounds of the invention are also useful for triggering ovulation, increasing spermatozoal motility or triggering uterine contractions.

The compounds of the present invention, which are preferably used in the form of their non-toxic addition salts, optionally in association with a physiologically acceptable excipient, will generally be prescribed in therapeutics at doses of about 0.1 mg/day to 200 mg/day in a form which can be administered by intravenous, intramuscular, subcutaneous or intra-arterial injection, transdermally or also topically in the form of gels or ointments.

The compounds of the present invention can also be formulated in association with active principles such as, for example, antitumoral or anti-infectious compounds, active compounds for the treatment of Alzheimer's disease, active compounds for the treatment of obesity, or any other active principle acting on the central or cerebral nervous system. In association with such active principles, they are useful for the treatment of pathological conditions of the central or cerebral nervous system.

The compounds of the present invention are also useful as pharmacological reagents, especially for the study of hormone-receptor interactions, or as diagnostic reagents in certain biological analyses such as the biological assay of the bradykinin $B_2$ receptor, on the one hand, and/or said bradykinin, on the other.

The compounds of formulae III, IV, VI, VII, VIII and IX, which serve as intermediates in the synthesis of the compounds of formula I, are novel products.

What is claimed is:

1. A pseudopeptide compound comprising a compound selected from the group consisting of:

(i) the compounds of formula I:

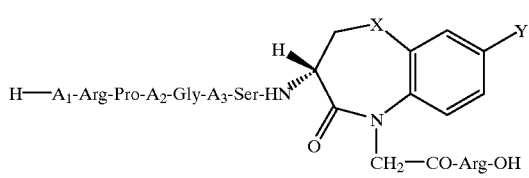

(SEQ. ID No. 1 and No. 2)

wherein
$A_1$ is a single bond, D-Arg or L-Lys,
$A_2$ is L-Pro or trans-4-hydroxy-L-Pro (4Hyp),
$A_3$ is L-Phe or L-thienylalanine (Thi),
Y is a hydrogen atom or a $C_1$–$C_3$-alkyl1 group, and
X is a sulfur or oxygen atom; and, (ii) addition salts thereof.

2. The compound according to claim 1 selected from the group consisting of:

H-D-Arg-Arg-Pro4Hyp-Gly-Thi-Ser-DBT(H)-Arg-OH (SEQ ID No. 3);
H-Lys-Arg-Pro4Hyp-Gly-Thi-Ser-DBT(H)-Arg-OH (SEQ ID No. 4);
H-Arg-Pro-Pro-Gly-Phe-Ser-DBT(H)-Arg-OH (SEQ ID No. 5);

H-D-Arg-Arg-Pro4Hyp-Gly-Thi-Ser-DBO(H)-Arg-OH (SEQ ID No. 6); and

H-D-Arg-Arg-Pro4Hyp-Gly-Thi-Ser-DBT(CH3)-Arg-OH (SEQ ID No.7);

wherein

Thi is thienylalanine,

DBO(H) residue of is the amino acid of the structure

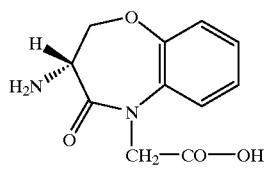

DBT(H) residue of is the amino acid of the structure

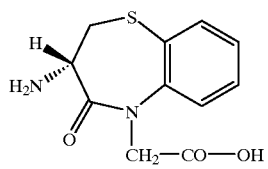

and DBT(CH3) residue of is the amino acid of the structure

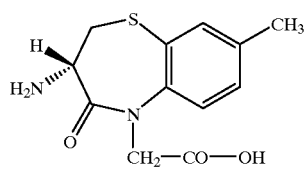

and acid addition salts thereof.

3. A method of treatment of pathological conditions involving bradykinin or its homologs, said method comprising administering to a patient in need of such a treatment a therapeutically effective amount of a compound of formula I or one of its non-toxic acid addition salts according to claim 1.

4. The method of treatment according to claim 3 wherein the pathological condition is myocardial ischemia.

5. The method of treatment according to claim 3 wherein the pathological condition relates to permeability of the blood-brain barrier.

6. The method of treatment according to claim 3 wherein the pathological condition relates to ovulation and uterine contraction triggering and spermatozoal motility.

7. The method of treatment according to claim 3 wherein the compound is administered intravenously, intramuscularly, subcutaneously or intra-arterial injection, transdermally, or topically.

8. The method of treatment according to claim 3 wherein the compound is administered at a dosage of about 0.1 mg/day to 200 mg/day.

9. The method of treatment according to claim 3 wherein the compound of formula I or one of its non-toxic salts is used in association with at least one other active principle for pathological conditions of the central or cerebral nervous system.

10. An assay method comprising using a compound of formula I or one of its acid addition salts according to claim 1 as a reagent for biologically assaying (i) bradykinin $B_2$ receptor, and/or (ii) said bradykinin.

11. A method for preparing a compound of formula I or one of its addition salts according to claim 1, said method comprising the steps of:

(1) reacting ethyl bromoacetate with a compound of the formula II:

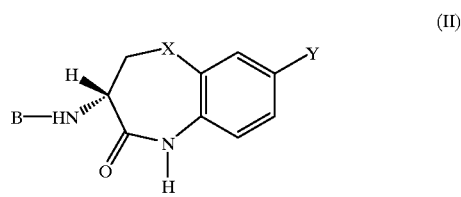

(II)

wherein

X is an oxygen atom or a sulfur atom,

B is an amino-protecting group of the oxycarbonyl type, and

Y is a hydrogen atom or a $C_1$–$C_3$ alkyl group;

in an inert solvent, in the presence of a base, at room temperature and for about 1 to 8 hours, to give a compound of formula III:

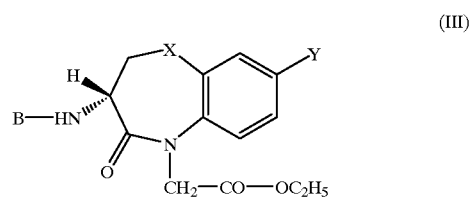

(III)

wherein B, X and Y are defined as indicated above;

(2) deprotecting the amine group of the compound of formula III thus obtained by reaction with hydrogen in the presence of a hydrogenation catalyst, under a hydrogen pressure of about $10^5$ to $5.10^5$ Pascals, to give a compound of formula IV:

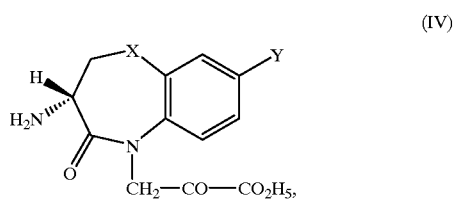

(IV)

wherein X and Y are defined as indicated above, (3) reacting the compound of formula IV, thus obtained with an L-serine product of the formula V:

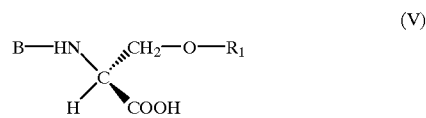

(V)

wherein:

B is defined as indicated above, and $R_1$ is a hydroxyl-protecting group;

in an inert solvent, at a temperature identical to or close to room temperature and for about 1 to 10 hours, to give a compound of formula VI:

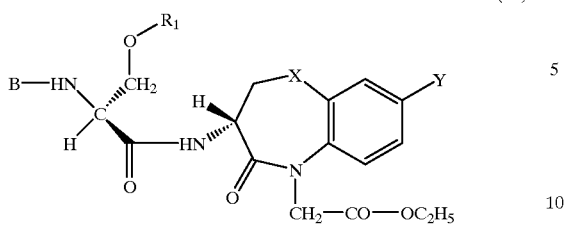

(VI)

wherein X, $R_1$, B and Y are defined as indicated above;

(4) hydrolyzing the ethyl ester group of the compound VI thus obtained, for about 1 to 5 hours, to give the compound of formula VII:

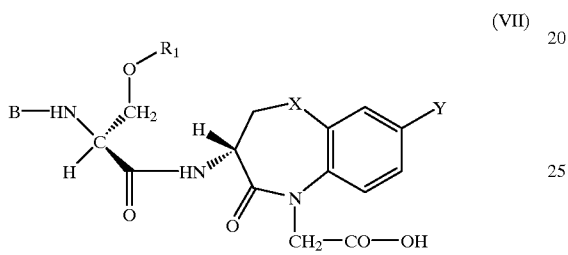

(VII)

wherein X, $R_1$, B and Y are defined as indicated above;

(5) reacting the compound of formula VII thus obtained with a Merrifield resin functionalized by an L-arginine (in which the basic side-group of Arg is protected by a tosyl group, the Arg residue being bonded to the resin by its C-terminal acid group) to give the grafted resin product of structure VIII:

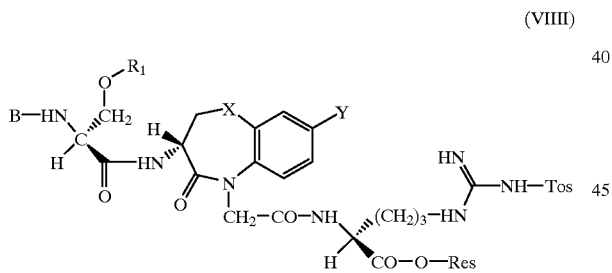

(VIIII)

wherein:
X is S or O,
Res is the resin,
B is an amino-protecting group,
$R_1$ is a hydroxyl-protecting group,
Y is a hydrogen atom or a $C_1$-$C_3$ alkyl group, and
Tos is the tosyl group;

(6) reacting the product of formula VIII thus obtained, by known methods of peptide synthesis, to regenerate the amine group at the N-terminal end of the serine, and then with an amino acid whose N-terminal amine group is protected by a group B and whose basic or hydroxyl side-group, when present, is protected, and repeating this procedure of deprotection/coupling with the appropriate amino acid as many times as is necessary to obtain the sequence of formula I, namely with the following amino acids in succession:
(a) B-Phe-OH or B-Thi-OH B-Gly-OH
(b) B-Pro-OH or B4Hyp-OH
(c) B-Pro-OH
(d) B-Arg($R_2$)-OH; and optionally,
(e) B-Lys($R_2$)-OH or B-D-Arg($R_2$)-OH to give a product of the formula Ia:
B-$Z_1$-Arg($R_2$)-Pro-A2-Gly-$A_3$-Ser($R_1$)-DBZ(Y)-Arg(Tos)-O-Res (1a)
wherein $A_2$, $A_3$, B, $R_1$ and Res are defined as indicated above;
$R_2$ is a protecting group for the basic side-group;
B, is a single bond, D-Arg($R_2$) or L-Lys($R_2$), and
DBZ(Y) represents the group

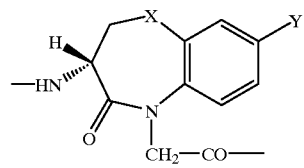

wherein X and Y being defined as indicated above;
(7) deprotecting the resulting compound of formula I and liberating it from the resin.
12. The method according to claim 11, comprising the steps of:
(1a) reacting ethyl bromoacetate with a compound of formula II:

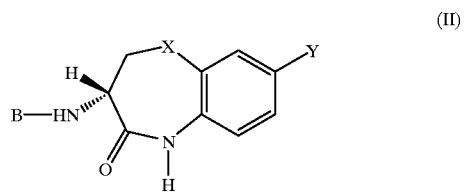

(II)

wherein X is S or O, and B and Y are defined as indicated above, under conditions analogous to those described in step (1) of claim 11, to obtain the compound of formula III:

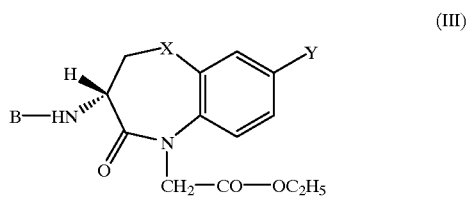

(III)

wherein X, B and Y are defined as indicated above;
(2a) carrying out the hydrolysis of the ester group of the compound of formula III thus obtained, under conditions analogous to those described in step (4) of claim 11, to provide the compound of formula IX:

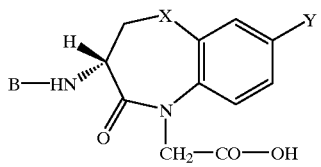

wherein X, B and Y are defined as indicated above; and (3a) continuing the synthesis of the compounds of the formula I, the compound of formula IX above being considered as an N-protected amino acid, to give the desired compound of the formula I after deprotection and separation from the support resin according to steps (6) and (7) of claim 11.

13. The method according to claim 11 wherein B is selected from the group consisting of alkoxycarbonyl, aryloxycarbonyl and heteroaryloxycarbonyl.

14. The method according to claim 11 wherein the inert solvent is selected from the group consisting of tetrahydrofuran, dichloromethane and N,N-dimethylformamide.

15. The method according to claim 11 wherein the hydrogenation catalyst is selected from the group consisting of palladium and barium sulfate.

16. The method according to claim 11 wherein the addition salt is a salt of an acid selected from the group consisting of mineral acid and organic acid.

17. The method according to claim 16 wherein the addition salt is a salt of an acid selected from the group consisting of hydrochloric, hydrobromic, phosphoric and sulfur acid.

18. The method according to claim 16 wherein the addition salt is a salt of an acid selected from the group consisting of methanesulfonic, maleic, fumaric oxalic, citric, acetic and trifluoroacetic acid.

19. The method according to claim 11 further comprising deprotecting the resulting compound with trifluoroacetic acid followed by second treatment of hydrogen fluoride.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION:3
      (D) OTHER INFORMATION:/note= "Pro means Pro or 4Hyp"

(ix) FEATURE:
      (A) NAME/KEY: Modified-site
      (B) LOCATION:5
      (D) OTHER INFORMATION:/note= "Xaa means Phe or
         thienylalanine"

(ix) FEATURE:
      (A) NAME/KEY: Modified-site
      (B) LOCATION:7
      (D) OTHER INFORMATION:/note= "Xaa means 3-amino-3,4-
         dihydro-8-Y-4-oxo-1,5-benzoxazepin-5(2H)-acetic
         acid [DBO(Y)] or 3-amino-3,4-dihydro-8-Y-4-oxo-
         1,5-benzothiazepin-5(2H)-acetic acid [DBT(Y)], wherein Y is H or C1-C3 alkyl"

(xi) SEQUENCE DESCRIPTION: SEQ ID NO: 1:

Arg Pro Pro Gly Xaa Ser Xaa Arg
1               5

(2) INFORMATION FOR SEQ ID NO: 2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "Xaa means D-Arg or L-Lys"

(ix) FEATURE:
        (A) NAME/KEY: Modified-site
        (B) LOCATION:4
        (D) OTHER INFORMATION:/note= "Pro means Pro or 4Hyp"

(ix) FEATURE:
        (A) NAME/KEY: Modified-site
        (B) LOCATION:6
        (D) OTHER INFORMATION:/note= "Xaa means Phe or
            thienylalanine"

(ix) FEATURE:
        (A) NAME/KEY: Modified-site
        (B) LOCATION:8
        (D) OTHER INFORMATION:/note= "Xaa means 3-amino-3,4-
            dihydro-8-Y-4-oxo-1,5-benzoxazepin-5(2H)-acetic
            acid [DBO(Y)] or 3-amino-3,4-dihydro-8-Y-
            4-oxo-1,5-benzothiazepin-5(2H)-acetic acid
            [DBT(Y)], wherein Y is H or C1-C3 alkyl"

(xi) SEQUENCE DESCRIPTION: SEQ ID NO: 2:

Xaa Arg Pro Pro Gly Xaa Ser Xaa Arg
1               5

(2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "Arg means D-Arg"

(ix) FEATURE:
        (A) NAME/KEY: Modified-site
        (B) LOCATION:4
        (D) OTHER INFORMATION:/note= "Pro means 4Hyp"

(ix) FEATURE:
        (A) NAME/KEY: Modified-site
        (B) LOCATION:6
        (D) OTHER INFORMATION:/note= "Xaa means thienylalanine"

(ix) FEATURE:
        (A) NAME/KEY: Modified-site
        (B) LOCATION:8
        (D) OTHER INFORMATION:/note= "Xaa means 3-amino-3,4-
            dihydro-4-oxo-1,5-benzothiazepin-5(2H)-acetic acid [DBT(H)]"

(xi) SEQUENCE DESCRIPTION: SEQ ID NO: 3:

Arg Arg Pro Pro Gly Xaa Ser Xaa Arg
1               5

(2) INFORMATION FOR SEQ ID NO: 4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:4
        (D) OTHER INFORMATION:/note= "Pro means 4Hyp"

(ix) FEATURE:
        (A) NAME/KEY: Modified-site
        (B) LOCATION:6
        (D) OTHER INFORMATION:/note= "Xaa means thienylalanine"

(ix) FEATURE:
        (A) NAME/KEY: Modified-site
        (B) LOCATION:8
        (D) OTHER INFORMATION:/note= "Xaa means 3-amino-3,4-
           dihydro-4-oxo-1,5-benzothiazepin-5(2H)-acetic
           acid [DBT(H)]"

(xi) SEQUENCE DESCRIPTION: SEQ ID NO: 4:

Lys Arg Pro Pro Gly Xaa Ser Xaa Arg
1               5

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:7
        (D) OTHER INFORMATION:/note= "Xaa means 3-amino-3,4-
           dihydro-4-oxo-1,5-benzothiazepin-5(2H)-acetic
           acid [DBT(H)]"

(xi) SEQUENCE DESCRIPTION: SEQ ID NO: 5:

Arg Pro Pro Gly Phe Ser Xaa Arg
1               5

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "Arg means D-Arg"

```
        (ix) FEATURE:
              (A) NAME/KEY: Modified-site
              (B) LOCATION:4
              (D) OTHER INFORMATION:/note= "Pro means 4Hyp"

(ix) FEATURE:
              (A) NAME/KEY: Modified-site
              (B) LOCATION:6
              (D) OTHER INFORMATION:/note= "Xaa means thienylalanine"

(ix) FEATURE:
              (A) NAME/KEY: Modified-site
              (B) LOCATION:8
              (D) OTHER INFORMATION:/note= "Xaa means 3-amino-3,4-
                  dihydro-4-oxo-1,5-benzoxazepin-5(2H)-acetic
                  acid [DBO(H)]"

(xi) SEQUENCE DESCRIPTION: SEQ ID NO: 6:

Arg Arg Pro Pro Gly Xaa Ser Xaa Arg
1                   5

(2) INFORMATION FOR SEQ ID NO: 7:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION:1
              (D) OTHER INFORMATION:/note= "Arg means D-Arg"

(ix) FEATURE:
              (A) NAME/KEY: Modified-site
              (B) LOCATION:4
              (D) OTHER INFORMATION:/note= "Pro means 4Hyp"

(ix) FEATURE:
              (A) NAME/KEY: Modified-site
              (B) LOCATION:6
              (D) OTHER INFORMATION:/note= "Xaa means thienylalanine"

(ix) FEATURE:
              (A) NAME/KEY: Modified-site
              (B) LOCATION:8
              (D) OTHER INFORMATION:/note= "Xaa means 3-amino-3,4-
                  dihydro-8-methyl-4-oxo-1,5-benzothiazepin-5(2H)-
                  acetic acid [DBT(Me)]"

(xi) SEQUENCE DESCRIPTION: SEQ ID NO: 7:

Arg Arg Pro Pro Gly Xaa Ser Xaa Arg
1                   5
```